United States Patent

McRea et al.

[11] Patent Number: 5,858,238
[45] Date of Patent: Jan. 12, 1999

[54] SALVAGE OF AUTOLOGOUS BLOOD VIA SELECTIVE MEMBRANE/SORPTION TECHNOLOGIES

[75] Inventors: James C. McRea, Salt Lake City; Stephanie Poulsen, Murray; Yong Nian Xia, Salt Lake City; Kirk Fowers, Layton, all of Utah

[73] Assignee: Baxter Research Medical, Inc., Midvale, Utah

[21] Appl. No.: 813,504

[22] Filed: Mar. 7, 1997

Related U.S. Application Data

[60] Provisional application No. 60/013,135 Mar. 8, 1996.

[51] Int. Cl.$^6$ .......................... B01D 61/00; B01D 61/58; B01D 36/00; A61M 1/34
[52] U.S. Cl. .......................... 210/645; 210/252; 210/253; 210/295; 210/321.6; 210/321.72; 210/321.78; 210/500.23; 210/650; 210/651; 210/653; 210/654; 210/655; 210/805; 210/806; 604/4; 604/5; 604/6
[58] Field of Search ...................... 210/644, 645, 210/650, 651, 653, 654, 655, 805, 806, 252, 253, 257.2, 255, 263, 321.6, 321.72, 323.1, 433.1, 500.23, 500.21, 321.78, 321.79, 321.8, 321.87, 321.88, 321.89; 435/174, 177, 178; 436/177, 178; 530/412, 414, 413, 810, 812, 813, 814; 604/4, 5, 6

[56] References Cited

U.S. PATENT DOCUMENTS

| | | |
|---|---|---|
| 4,071,444 | 1/1978 | Ash et al. . |
| 4,348,283 | 9/1982 | Ash .......................................... 210/356 |
| 4,581,141 | 4/1986 | Ash .......................................... 210/502 |
| 4,661,246 | 4/1987 | Ash .......................................... 210/87 |
| 4,995,268 | 2/1991 | Ash .......................................... 210/87 |
| 5,211,850 | 5/1993 | Shettigar et al. ........................ 210/645 |
| 5,277,820 | 1/1994 | Ash .......................................... 210/646 |
| 5,536,412 | 7/1996 | Ash .......................................... 210/645 |

OTHER PUBLICATIONS

J. Boldt, et al, *Blood Conservation in Cardiac Operations—Cell Separation Versus Hemofiltration*, J. Thorac. Cardiovasc. Surg. (1989), 97:832–40.

Y. Nakamura, et al, *Comparative Study of Cell Saver and Ultrafiltration Nontransfusion in Cardiac Surgergy*, Ann. Thorac. Surg. (1990), 49:973–8.

J. Boldt, et al, *Six Different Hemofiltration Devices for Blood Conservation in Cardiac Surgery*, Ann. Thorac. Surg. (1991), 51:474–53.

D. Tixier, et al, *Blood Saving in Cardiac Surgery: Simple Approach and Tendencies*, Perfusion (1991), 6:265–273.

Y. Iu, et al, *Maximizing Blood Conservation in Cardiac Surgery*, Perfusion Life (Jul. 1994), 14–18.

R. Breyer, et al, *A Comparison of Cell Saver Versus Untrafilter During Coronary Artery Bypass Operations*, J. Thorac. Cardiovasc. Surg. (1985), 90:736–740.

(List continued on next page.)

*Primary Examiner*—John Kim
*Attorney, Agent, or Firm*—Workman, Nydegger & Seeley

[57] ABSTRACT

Methods and apparatuses for salvaging blood from a patient are disclosed. A blood salvaging and/or blood processing circuit coupled to a cardiopulmonary bypass circuit, cardiotomy circuit, or directly to the patient comprises a hemocentrator for removing water, fluids, and low molecular weight solutes by ultrafiltration and a sorbent-containing plasma separator for removing a selected solute, such as heparin. A combination device for salvaging blood comprises a closed plasma chamber containing a plasma chamber solution, a hollow fiber plasma-separating membrane for receiving blood and permitting plasma to be transported therethrough into the plasma chamber solution and for refiltering the treated plasma back into the blood circuit, a selective sorbent for contacting the selected solute in the plasma and binding the selected solute, and an ultrafiltration membrane for removing water, fluids, and low molecular weight components from the plasma.

42 Claims, 5 Drawing Sheets

OTHER PUBLICATIONS

P. Page, *Ultrafiltration Versus Cell Washing for Blood Concentration,* J. Extra–Corp. Tech. (1990), vol. 22, 3:142–150.

H. Johnson, et al, *Comparative Analysis of Recovery of Cardiopulmonary Bypass Residual Blood: Cell Saver vs. Hemoconcentrator,* J. Extra–Corp. Tech. (1994), vol. 26, 4:194–199.

J. Morris & Y. Tan, *Autotransfusion: Is There a Benefit in a Current Practice of Aggressive Blood Conservation?* Ann. Thorac. Surg. (1994), 58:502–8.

Mohammad, et al, *Quantative Removal of Heparin from Plasma and Other Aqueous Solutions by Affinity Adsorption on Poly(L)lysine Sepharose 4B,* Thrombosis Res. (1980), 20:599–609.

SALVAGE OF AUTOLOGOUS BLOOD VIA SELECTIVE MEMBRANE/SORPTION TECHNOLOGIES

CROSS-REFERENCE TO RELATED APPLICATIONS

This application claims the benefit of U.S. Provisional Application No. 60/013,135, filed Mar. 8, 1996.

BACKGROUND OF THE INVENTION

This invention relates to a system and method for salvaging or recovering blood to reduce net blood loss during surgery or other medical procedure and selectively removing solutes from plasma. More particularly, the invention relates to a system and method for removing excess water and/or fluid from whole blood or plasma and selectively removing solutes, such as drugs (e.g. heparin), autoantibodies, toxins, antigens, plasma components, and lipids (e.g. cholesterol) from plasma such that the treated blood can be administered directly to the patient or saved for later administration.

A patient undergoing major cardiac surgery with cardiopulmonary bypass (CPB) can lose a significant amount of blood. If the blood loss is profuse, the patient may require the administration of homologous blood products. Homologous blood products can sometimes be in short supply and may carry blood-borne pathogens.

To reduce the amount of blood loss during surgery and thus the need for administration of homologous blood products, several methods of intraoperative blood salvage or autotransfusion have been tried. These methods include administration of drugs (e.g. aprotinin, $\epsilon$-amino caproic acid), hemoconcentration, modified ultrafiltration, cell washing, autologous predonation of blood for perioperative reinfusion, and autotransfusion of processed shed blood. J. Boldt et al., Blood Conservation in Cardiac Operations—Cell Separation Versus Hemofiltration, 97 J. Thorac. Cardiovasc. Surg. 832 (1989); Y. Nakamura et al., Comparative Study of Cell Saver and Ultrafiltration Nontransfusion in Cardiac Surgery, 49 Ann. Thorac. Surg. 973 (1990); J. Boldt et al., Six Different Hemofiltration Devices for Blood Conservation in Cardiac Surgery, 51 Ann. Thorac. Surg. 747 (1991); D. Tixier et al., Blood Saving in Cardiac Surgery: Simple Approach and Tendencies, 6 Perfusion 265 (1991); Y. Iu et al., Maximizing Blood Conservation in Cardiac Surgery, Perfusion Life 14 (July 1994); R. Breyer et al., A Comparison of Cell Saver Versus Ultrafilter During Coronary Artery Bypass Operations, 90 J. Thorac. Cardiovasc. Surg. 736 (1985); P. Page, Ultrafiltration Versus Cell Washing for Blood Concentration, 22 J. Extra-Corp. Tech. 142 (1990); H. Johnson et al., Comparative Analysis of Recovery of Cardiopulmonary Bypass Residual Blood: Cell Saver vs. Hemoconcentrator, 26 J. Extra-Corp. Tech. 194 (1994); J. Morris & Y. Tan, Autotransfusion: Is There a Benefit in a Current Practice of Aggressive Blood Conservation?, 58 Ann. Thorac. Surg. 502 (1994). Of these techniques, hemoconcentration and cell washing are among the most commonly encountered.

Hemoconcentration or ultrafiltration extracts water and low molecular weight solutes from the plasma fraction of whole blood. Plasma proteins, including proteins involved in the coagulation cascade, remain relatively intact. Hemoconcentrators are generally small, compact, cost-effective, and can be added to an existing CPB circuit without major modifications. A disadvantage of hemoconcentration is that debris cannot be removed, thus shed blood collected during surgery cannot be processed through a hemoconcentrator unless it has first been filtered, i.e. through a cardiotomy reservoir. Moreover, hemoconcentration does not remove heparin from the blood, thus even though water has been removed, the blood remains fully heparinized. Another disadvantage is that plasma-free hemoglobin, which results from hemolysis and is known to be toxic to the kidneys, is not effectively removed by hemoconcentration filters.

Cell washing is a method of blood concentration wherein whole blood is subjected to centrifugation while being rinsed with a saline solution. Cell washing removes debris, plasma-free hemoglobin, and heparin, thus the method can be used on shed blood as well as blood remaining in the CPB circuit and cardiotomy reservoir. A major disadvantage of cell washing is that all of the plasma proteins, including coagulation proteins, are discarded. Platelets are lost as well. Further, cell washing requires that a separate system, including a centrifuge, be dedicated for such a procedure. Therefore, the process of cell washing is more expensive than hemoconcentration. Moreover, since coagulation proteins are removed in the process, it is sometimes necessary to administer replacement factors after cell washing.

Shettigar et al., U.S. Pat. No. 5,211,850, describes a plasma membrane sorbent system for removal of solutes from blood. The system comprises a bundle of U-shaped hollow fibers immersed in an electrolyte solution with a sorbent contained in a closed plasma chamber. As blood flows through the entry arm, plasma filtration into the plasma chamber occurs. Solutes in the plasma are selectively depleted in the plasma chamber through binding to the sorbents. The purified plasma then reenters the membrane by reverse filtration.

S. Ash et al., U.S. Pat. No. 4,071,444, discloses a portable "flat plate" reactor for use as an artificial kidney. The device comprises a sealed outer casing that is divided internally by a series of flexible membranes into chambers adapted to receive blood and other chambers adapted to receive a solution containing water, activated charcoal, zirconium phosphate, zirconium oxide and urease or other sorbents for absorbing the urea and creatinine drawn through the membrane from the blood.

S. Ash, U.S. Pat. No. 4,348,283, describes a dialyzer for use as an artificial kidney or extracorporeal mass transfer device. The device comprises a plurality of dialyzer units, each unit comprising a pair of semipermeable membranes spaced apart by a gasket such that a blood chamber is formed between the membranes. Spacers are used to separate the dialyzer units and support the membranes. The spaces between the dialyzer units form dialysis chambers, which contain a suspension of sorbents, such as activated charcoal, calcium-sodium loaded zeolites, and/or urease.

S. Ash, U.S. Pat. No. 4,581,141, teaches a dialysis material and method for removing uremic substances, wherein the dialysis material comprises an aqueous slurry containing charcoal, a highly calcium-loaded zeolite cation exchanger, a purified urease, a suspending agent such as methylcellulose, and an aliphatic carboxylic acid resin in the acid form.

S. Ash, U.S. Pat. No. 4,661,246, discloses a dialysis instrument with a pump on the dialysate side of the instrument for moving blood through the instrument. The instrument contains a sorbent column for purification of the dialysate, the sorbent column containing activated charcoal, immobilized urease, zirconium phosphate cation exchanger, and zirconium oxide anion exchanger.

S. Ash, U.S. Pat. No. 5,277,820, describes a device and method for extracorporeal treatment of blood for the removal of toxins. A sorbent suspension is used for removing such toxins wherein the sorbent comprises a powdered surface adsorptive agent such as activated charcoal, physiological electrolytes, a cation exchanger for removing ammonium ions and the like, and macromolecular flow inducing agents such as polyoxyalkylene derivatives of propylene glycol or polyvinylpyrrolidone. Cisplatin and methotrexate could be removed from the blood by this method.

These apparatuses and methods all lack the ability to be used for both hemoconcentration and removal of selected solutes from the blood.

In view of the foregoing, it will be appreciated that development of a system and process that removes excess water and/or fluid from whole blood or plasma, conserves plasma proteins including coagulation proteins, reduces and/or removes plasma-free hemoglobin and heparin and other targeted molecules, is cost effective, and is easily used and incorporated into an existing CPB circuit or in parallel with a CPB circuit, in contrast to the prior art where expensive, stand-alone devices are used and perhaps require additional personnel to operative them, would be a significant advancement in the art.

BRIEF SUMMARY OF THE INVENTION

It is an object of the present invention to provide a system and method for conserving blood during cardiac surgery or other medical procedure where blood loss can be copious.

It is also an object of the invention to provide a system and method for removing excess water and/or fluid from whole blood or plasma, wherein plasma proteins, including coagulation proteins, can be conserved.

It is another object of the invention to provide a system and method for conserving blood during cardiac surgery or other medical procedure where blood loss can be copious wherein selected solutes, such as heparin, plasma free hemoglobin, and selected proteins or hormones that have been activated, are reduced or removed.

It is still another object of the invention to provide a system and method for conserving blood during cardiac surgery wherein such system and method are cost effective, easy to use, and can be incorporated into an existing CPB circuit.

These and other objects can be accomplished by providing a system for salvaging blood from a patient for the selective removal of a targeted solute in the blood and the removal of water, fluids, and low molecular weight solutes comprising:

(a) a hemoconcentrator comprising a porous ultrafiltration membrane having a selected molecular weight cut-off for retaining components selected from the group consisting of cells and solutes with a molecular weight greater than the cut-off and for allowing water, fluids, and solutes with a molecular weight less than the cut-off to be removed from blood or plasma; and (b) a first solute removal device for selectively removing the targeted solute from blood by means of convective and diffusive transport of plasma from the blood across a hollow fiber plasma-separating membrane into a plasma chamber where the selective removal of the targeted solute from non-targeted solutes using a sorbent is accomplished followed by the subsequent transport of the non-targeted solutes across the plasma-separating membrane back into the blood, comprising
(i) a closed plasma chamber configured for being filled with a plasma chamber solution and to freely circulate, equilibrate, and interact plasma in the plasma chamber solution under relatively uniform pressure;
(ii) the hollow fiber plasma-separating membrane, wherein the plasma-separating membrane has an inlet arm and an outlet arm and is configured for being immersed in the plasma chamber solution in the closed plasma chamber;
(iii) at least one sorbent having an affinity for binding the targeted solute, wherein the sorbent is contained in the closed plasma chamber;
(iv) means for securing the inlet arm and outlet arm of the plasma-separating membrane in the plasma chamber and closing the chamber to maintain relatively uniform plasma chamber solution pressure; and
(v) means for circulating the blood into the inlet arm, through the plasma-separating membrane, and out through the outlet arm; and (c) means for coupling the hemoconcentrator to the first solute removal device to permit liquid communication therebetween and for coupling the hemoncentrator and the first solute removal device to the patient to permit blood to be received from and returned to the patient.

Preferably, the porous ultrafiltration membrane of the hemoconcentrator comprises a plurality of hollow fibers having a molecular weight cut-off in the range of about 10,000 to 100,000. Preferred materials include polyacrylonitrile, polysulfone, polynethylmethacrylate, cellulose acetate, cellulose diacetate, and cellulose triacetate.

Preferably, the hollow fiber plasma-separating membrane comprises a bundle of parallel hollow fibers constructed of a blood-compatible material having a suitable pore size to allow passage of plasma into the plasma chamber solution while retaining blood cells and platelets from the blood within the hollow fibers. It is preferred that pore sizes in the plasma-separating membrane range between about 0.01 $\mu$m to 1.0 $\mu$m and the plasma-separating membrane is made from a material selected from the group consisting of polypropylene, cellulose diacetate, polycarbonate, polyvinylchloride, polyvinylalcohol, polymethylmethacrylate, polyethylene, polysulfone, and polyethylenevinylalcohol.

The sorbent should be of a size and configuration such that said sorbent is not permeable to the plasma-separating membrane. The sorbent comprises a ligand immobilized on a substrate wherein the ligand is preferably a member selected from the group consisting of enzymes, living tissue, fragments of tissue, cells, antibodies, peptides, macromolecules, nucleic acids, lectins, carbohydrates, and chelating agents. In preferred embodiments, the sorbent has affinity for heparin and the substrate is agarose. In an especially preferred embodiment, the sorbent is poly-L-lysine-coupled agarose.

The hemoconcentrator and solute removal device can be configured for simultaneous hemoconcentration and removal of the targeted solute or for sequential hemoconcentration and removal of the targeted solute. The system can also be configured such that hemoconcentration, i.e. removal of water, fluids, and low molecular weight solutes, is carried out in the blood or in the plasma. To remove water, fluids, and low molecular weight solutes from the plasma, the porous ultrafiltration membrane can be placed in the plasma chamber of the solute removal device or a second solute removal device can be added to the system, wherein the hemoconcentrator is placed to interconnect the two plasma chambers.

Thus, an apparatus for selectively removing a targeted solute from blood by binding the targeted solute to an affinity sorbent and removing water, fluids, and low molecular weight solutes by ultrafiltration comprises:

(a) a closed plasma chamber configured for being filled with a plasma chamber solution and to freely circulate, equilibrate, and interact plasma in the plasma chamber solution under relatively uniform pressure;

(b) a hollow fiber plasma-separating membrane having an inlet arm and an outlet arm and configured for being immersed in the plasma chamber solution in the closed plasma chamber;

(c) at least one sorbent having an affinity for binding the targeted solute, wherein the sorbent is contained in the closed plasma chamber;

(d) means for securing the inlet arm and outlet arm of the plasma-separating membrane in the plasma chamber and closing the chamber to maintain relatively uniform plasma chamber solution pressure; and (e) a porous ultrafiltration membrane disposed in the closed plasma chamber and configured for being immersed in the plasma chamber solution, the ultrafiltration membrane having a selected molecular weight cut-off for allowing water, fluids, and solutes with a molecular weight lower than the cut-off to pass therethrough and for retaining solutes with a molecular weight greater than the cut-off and means for withdrawing the water, fluids, and solutes that pass through the ultrafiltration membrane; and (f) means for circulating the blood into the inlet arm such that plasma, including water, fluids, and low molecular weight solutes therein, is transported from the blood across the plasma-separating membrane by convective and diffusive transport into the plasma chamber solution where the selective removal of the targeted solute from non-targeted solutes using the affinity sorbent is accomplished followed by the subsequent transport of the non-targeted solutes across the membrane back into the blood and out through the outlet arm.

Moreover, a system for salvaging blood from a patient for the selective removal of a targeted solute in the blood and the removal of water, fluids, and low molecular weight solutes comprises:

(a) a hemoconcentrator comprising an inlet port, an outlet port, and a porous ultrafiltration membrane having a selected molecular weight cut-off for retaining components selected from the group consisting of cells and solutes with a molecular weight greater than the cut-off and for allowing water, fluids, and solutes with a molecular weight less than the cut-off to be removed from blood or plasma; and (b) first and second solute removal devices for selectively removing the targeted solute from blood by means of convective and diffusive transport of plasma from the blood across a hollow fiber plasma-separating membrane into a plasma chamber where the selective removal of the targeted solute from non-targeted solutes using a sorbent is accomplished followed by the subsequent transport of the non-targeted solutes across the plasma-separating membrane back into the blood, each first and second solute removal device comprising (i) a closed plasma chamber configured for being filled with a plasma chamber solution and to freely circulate, equilibrate, and interact plasma in the plasma chamber solution under relatively uniform pressure;

(ii) the hollow fiber plasma-separating membrane, wherein the plasma-separating membrane has an inlet arm and an outlet arm and is configured for being immersed in the plasma chamber solution in the closed plasma chamber;

(iii) at least one sorbent having an affinity for binding the targeted solute, wherein the sorbent is contained in the closed plasma chamber;

(iv) means for securing the inlet arm and outlet arm of the plasma-separating membrane in the plasma chamber and closing the chamber to maintain relatively uniform plasma chamber solution pressure; and (v) means for circulating the blood into the inlet arm, through the plasma-separating membrane, and out through the outlet arm;

(c) means for coupling the plasma chamber of the first solute removal device to the inlet port of the hemoconcentrator and means for coupling the outlet port of the hemoconcentrator to the plasma chamber of the second solute removal device such that plasma can flow from the first solute removal device through the hemoconcentrator to the second solute removal device such that water, fluids, and low molecular weight solutes can be removed from the plasma by ultrafiltration, and means for coupling the outlet arm of the first solute removal device to the inlet arm of the second solute removal device such that blood can flow therebetween; and (d) means for coupling the first and second solute removal devices to the patient to permit blood to be received from and returned to the patient.

A method of selectively removing a targeted solute and water, fluids, and low molecular weight solutes from blood comprises:

(a) providing a system comprising:

(1) a hemoconcentrator comprising a porous ultrafiltration membrane having a selected molecular weight cut-off for retaining components selected from the group consisting of cells and solutes with a molecular weight greater than the cut-off and for allowing water, fluids, and solutes with a molecular weight less than the cut-off to be removed from blood or plasma; and (2) a first solute removal device for selectively removing the targeted solute from blood by means of convective and diffusive transport of plasma from the blood across a hollow fiber plasma-separating membrane into a plasma chamber where the selective removal of the targeted solute from non-targeted solutes using a sorbent is accomplished followed by the subsequent transport of the non-targeted solutes across the plasma-separating membrane back into the blood, comprising (i) a closed plasma chamber configured for being filled with a plasma chamber solution and to freely circulate, equilibrate, and interact plasma in the plasma chamber solution under relatively uniform pressure;

(ii) the hollow fiber plasma-separating membrane, wherein the plasma-separating membrane has an inlet arm and an outlet arm and is configured for being immersed in the plasma chamber solution in the closed plasma chamber;

(iii) at least one sorbent having an affinity for binding the targeted solute, wherein the sorbent is contained in the closed plasma chamber;

(iv) means for securing the inlet arm and outlet arm of the plasma-separating membrane in the plasma chamber and closing the chamber to maintain relatively uniform plasma chamber solution pressure; and (v) means for circulating the blood into the inlet arm, through the plasma-separating membrane, and out through the outlet arm; and (3) means for coupling the hemoconcentrator to the first solute removal device to permit liquid communication therebetween and for coupling the hemoncentrator and the first solute removal device to the patient to permit blood to be received from and returned to the patient;

(b) directing the blood from a source into the inlet arm by the means for circulating the blood, through the plasma-separating membrane and out the outlet arm at a volume and a velocity that permits convective and diffusive transport of plasma from the blood across the plasma-separating membrane along the inlet arm of the plasma-separating membrane into the plasma chamber solution;

(c) causing the plasma in the plasma chamber solution to come into contact with the sorbent such that the targeted solute is selectively bound to the sorbent;

(d) causing the non-targeted solutes to pass by diffusive and convective transport from the plasma chamber solution across the plasma-separating membrane into the blood retained by the plasma-separating membrane and out of the device;

(e) causing the blood or plasma to pass through the hemoconcentrator such that water, fluids, and solutes with a molecular weight less than the cut-off pass through the porous ultrafiltration membrane and are withdrawn from the blood or plasma, and the ultrafiltration membrane retains cells and solutes with a molecular weight greater than the cut-off in the blood or plasma.

DETAILED DESCRIPTION

Before the present system and method for salvaging or recovering autologous blood are disclosed and described, it is to be understood that this invention is not limited to the particular embodiments, process steps, and materials disclosed herein as such embodiments, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. For example, reference to "a solute" includes reference to two or more of such solutes, and reference to a device comprising "a sorbent" includes reference to a device comprising one or more or such sorbents.

In describing and claiming the present invention, the following terminology will be used in accordance with the definitions set out below.

As used herein, "patient" refers to a human or a warm-blooded animal.

As used herein, "patient blood" refers to blood taken directly from a patient, such as blood collected by predonation for storage and eventual administration to the patient.

As used herein, "circuit blood" refers to blood that is circulated through the CPB circuit. Circuit blood is typically given back to the patient before the end of surgery or shortly thereafter.

As used herein, "shed blood" refers to blood that is lost during surgery. Shed blood is aspirated from the body and stored in a cardiotomy reservoir.

As used herein, "peptide" means peptides of any length and includes proteins.

Blood consists of cellular and non-cellular fractions, or, alternatively, of formed and non-formed elements. As used herein, "plasma" means the non-cellular fraction or non-formed elements of blood. In other words, plasma means the portion of blood exclusive of the cellular fraction or formed elements thereof.

As used herein, "sorbent" means a ligand coupled to a substrate. Sorbents can be in any usable form of sufficient size that the sorbent is not permeable to the plasma-separating membrane of the solute removal device, i.e. does not enter the blood. For example, sorbents can be in particulate form, such as beads, spheres, or the like. Sorbents can also be present as filaments, strands, sheets, or films. The form is not important as long as there is adequate opportunity for the circulation of plasma and contact between the sorbent and the plasma. Suitable substrates include biocompatible polymers, such as agarose, polyacrylamide, nylon, nitrocellulose, polystyrene, and the like. The substrate should have functional groups to which the ligand can be attached according to principles and materials well known in the art. Suitable ligands include antibodies, peptides, enzymes, nucleic acids, lectins, carbohydrates, chelating agents, macromolecular ligands, and the like.

As used herein, "plasma chamber solution" means the solution contained in the plasma chamber. At the beginning of a separation procedure, the initial solution will typically comprise water or an electrolyte, i.e. saline, solution containing sorbents and other selected materials. As the various plasma components enter the plasma chamber by convection or diffusion from the hollow fiber plasma-separating membrane, equilibration will take place such that, except for the targeted components bound to the sorbent in the plasma chamber, the concentration of plasma components in the blood inside the lumens of the hollow fibers will be the same as the concentration of the plasma components in the plasma chamber. Hence, the makeup of the plasma chamber solution can vary during the removal process, but functionally the action composition is not critical.

Figure 1:
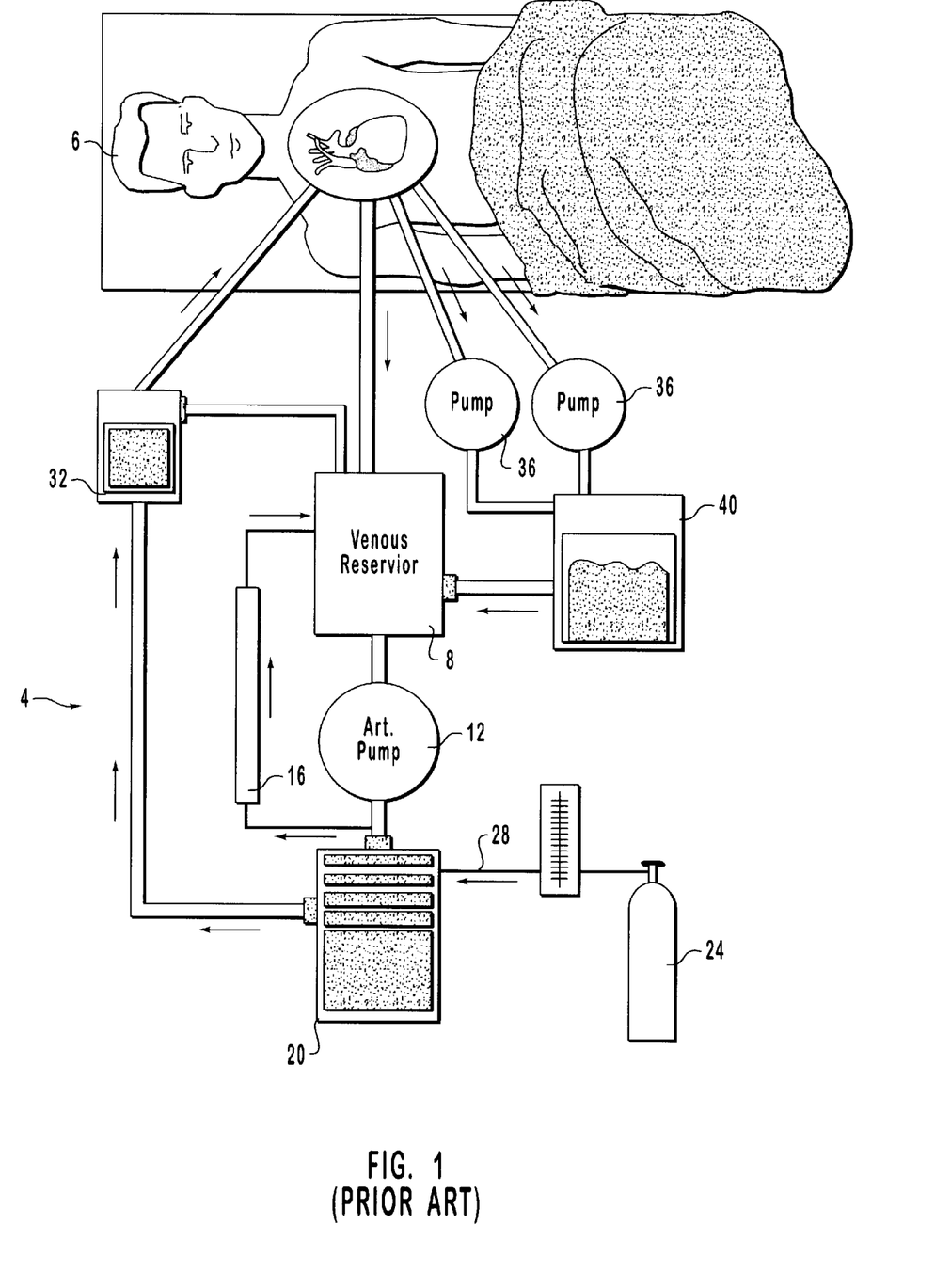
FIG. 1 shows a schematic diagram of a CPB circuit according to the prior art.

Referring to FIG. 1, there is shown a schematic representation of a CPB circuit 4. Venous blood is removed from the patient 6 and conducted by gravity flow to a venous or CPB circuit blood reservoir 8. Blood is pumped out of the CPB reservoir 8 by a pump 12. This blood optionally can be circulated through a hemoconcentrator 16 for removing water, fluids, and low molecular weight molecules. Blood that has passed through the hemoconcentrator is returned to the venous reservoir 8. Blood can also be pumped through an oxygenator 20 for supplying oxygen to the blood. The oxygenator 20 is coupled to a source of oxygen 24 through an oxygen line 28. The oxygenator 20 is coupled to an arterial filter 32 for filtering the oxygenated blood before it is recirculated into the CPB circuit reservoir 8 or returned to the patient 6. Shed blood is removed from the patient 6 by means of a pump 36 and stored in a cardiotomy reservoir 40, where the shed blood is filtered. The cardiotomy reservoir 40 is coupled to the CPB circuit reservoir 8 such that filtered shed blood can selectively be mixed with CPB circuit blood.

Figure 2:
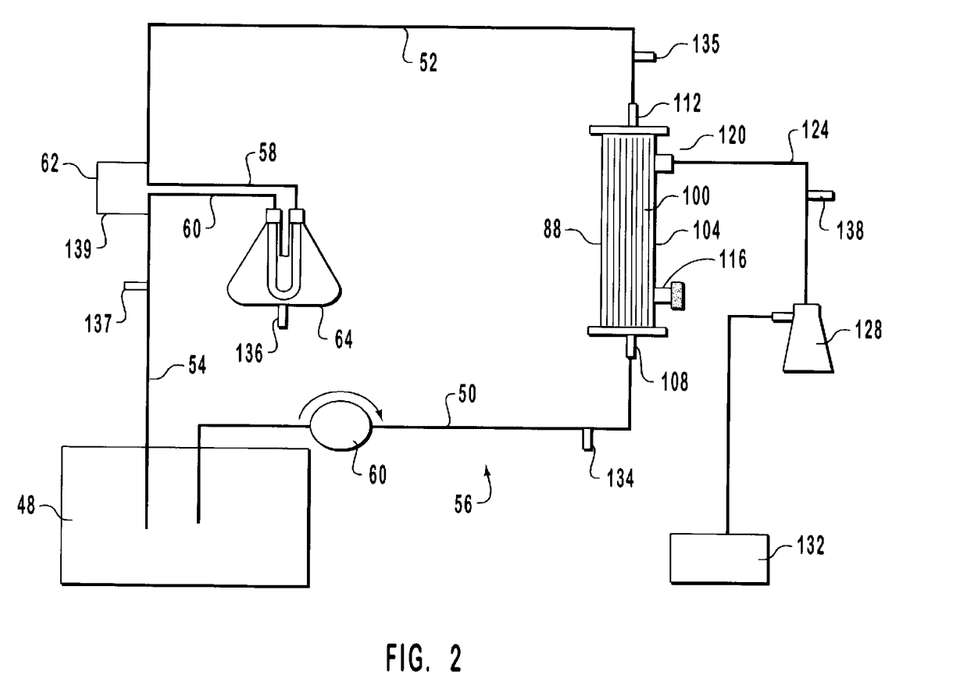
FIG. 2 shows a schematic diagram of an illustrative embodiment of a blood salvage circuit according to the present invention comprising a hemoconcentrator and a solute removal device.
Figure 3:
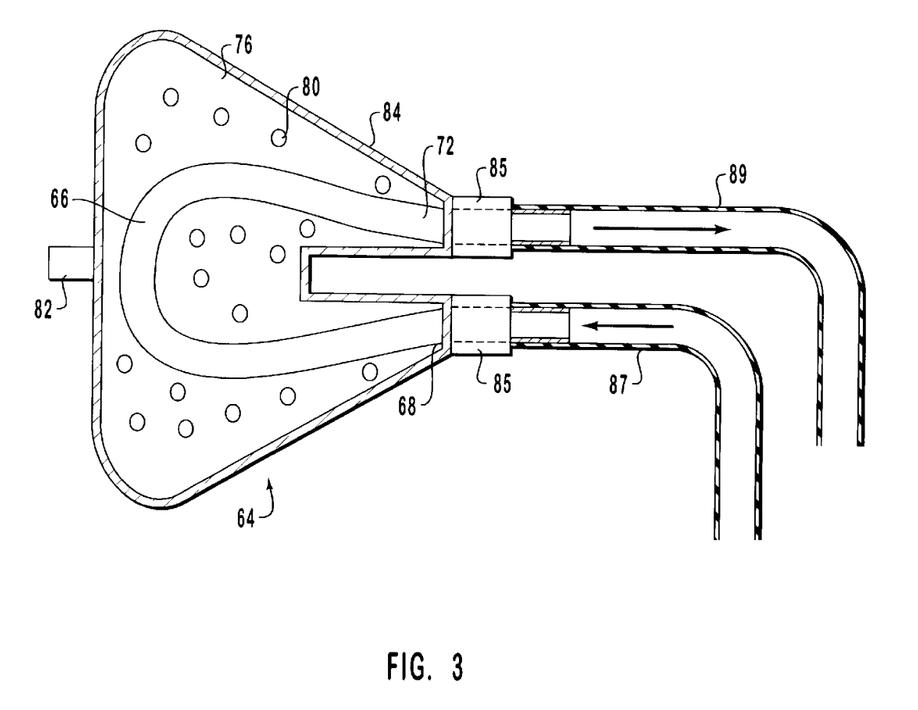
FIG. 3 shows a schematic diagram of a solute removal device according to the present invention.

FIG. 2 shows an embodiment of the present invention comprising a CPB circuit blood reservoir or cardiotomy reservoir or patient 48 coupled to a blood salvage circuit 56. The blood salvage circuit comprises a pump 60 for pumping the blood out of the reservoir 48 and moving it through the blood salvage circuit. The blood salvage circuit further comprises a hemoconcentrator 88 for removing water and low molecular weight solutes from the blood and a solute removal device 64 for separating plasma from the blood and contacting the separated plasma with a specific sorbent for removing a selected solute. Such a device is described in U.S. Pat. No. 5,211,850, which is hereby incorporated by reference, and is shown in FIG. 3. Line 50 couples the blood reservoir 48 to the hemoconcentrator 88, line 52 couples the hemoconcentrator to the solute removal device, and line 54 couples the solute removal device to the blood reservoir 48.

Referring now to FIG. 3, the solute removal device 64 comprises a bundle of hollow fibers that make up a hollow fiber plasma-separating membrane 66. Each hollow fiber has a central lumen through which the whole blood passes from the inlet arm 68 to the outlet arm 72 of the sorbent removal device. Each hollow fiber membrane has a series of pores or openings through which plasma and plasma components, toxins, drugs, or other solutes having diameters smaller than the pores can pass into a surrounding plasma chamber solution 76 containing a sorbent 80. The hollow fiber plasma-separating membrane 66, plasma chamber solution 76, and sorbent 80 are contained in a housing 84. The housing is closed by fixed potting material 85 and 86. The inlet arm of the plasma-separating membrane is coupled to an inlet line 87, and the outlet arm is coupled to an outlet line 89. Optionally, a plasma port 82 in the housing permits access to the plasma chamber for removing plasma therefrom, for making pressure measurements, adding sorbent or plasma chamber solution, or the like. The plasma may contain various sugars, proteins, hormones, antibodies, fats, bile salts, toxins, electrolytes, and the like, as well as other substances that may have been administered for various purposes. Heparin, for example, is added to the patient for its anticoagulation properties, but is desirably removed or inactivated at the end of CPB. When heparin and other small solutes exit the membranes through the pores by convection (pressure gradients) or diffusion, they enter into the plasma chamber solution 76 containing sorbent particles 80 that have a specificity for binding heparin or other selected solutes.

The hollow fiber plasma-separating membrane can be made of any blood compatible material having suitable pore size to allow passage of selected solute materials into the plasma chamber, even those of high molecular weight, and yet retain the blood cells and platelets in the lumen of the hollow fiber. Pore sizes in the membrane are relatively large, with sizes ranging between about 0.01 $\mu$m to 1.0 $\mu$m being suitable, with pore sizes of about 0.1 $\mu$m to 0.8 $\mu$m being preferred and pore sizes of about 0.4 to 0.75 $\mu$m most preferred. Exemplary of suitable fiber materials are polypropylene, cellulose diacetate, polycarbonate, polyvinylchloride, polyvinylalcohol, polymethylmethacrylate, polyethylene, polyethylenevinylalcohol, polysulfone, and the like.

The hollow fiber plasma-separating membrane dimensions (hollow fiber lumen diameter, length of each hollow fiber, and the number of fibers) and the blood flow rate through the fiber have to be optimized based on the art of membrane plasma separation. It is well known in the art of membrane plasma separation that the plasma separation rate is directly proportional to the blood shear rate and the transmembrane pressure. Damage to the blood cells, however, may occur if the transmembrane pressure is increased beyond a particular limit. Also, blood cells are susceptible to high shear rate. For a given blood flow rate and total membrane surface area, transmembrane pressure increases with the increase in hollow fiber length and with the decrease in lumen size. Shear rate also increases with the decrease in lumen size. The above-mentioned factors may be considered in arriving at the optimum size of the hollow fiber membrane. The removal rates of solutes from the blood depend on the plasma separation rate, the amount (surface area, etc.), affinity of sorbents, and the extent of plasma-sorbent interaction. Hollow fibers of the plasma-separating membrane having inside diameters of between about 150 $\mu$m and 500 $\mu$m and wall thicknesses of between about 50 $\mu$m to 400 $\mu$m are typical. The internal surface area of a typical plasma-separating membrane can be between about 0.1 and 5.0 $m^2$, and the volume of the plasma chamber can be between about 50 and 1000 ml. The length of the plasma-separating membrane from the inlet port to the exit port should be between about 10 and 100 cm, with lengths of about 20 to 25 cm being preferred. Flow rates of blood through the plasma-separating membrane can vary from about 50 to 3000 ml/min.

The plasma chamber should be sized to hold an adequate amount of sorbent materials to adsorb the unwanted solutes, such as heparin. This may vary depending on the medical procedure for which the blood salvage system is being used and the amount of heparin or other material to be removed and the nature of the sorbent material.

An illustrative commercial device according to FIG. 3 is a heparin removal device (HRD, Research Medical Inc., Midvale, Utah). This unit is a disposable hollow fiber membrane-type plasma separator consisting of a microporous polypropylene hollow fiber bundle mounted in polyurethane exit ports and a polystyrene plastic housing. Blood enters the fiber bundle through the blood inlet port, passes through the hollow fiber lumens in which a positive transmembrane pressure allows plasma to pass through the porous hollow fiber membrane along its entire length into the plastic housing where it contacts the sorbent. Solutes in the plasma with an affinity for the sorbent bind to the sorbent and are immobilized. The plasma with a reduced concentration of the selected solute can then be removed from the plasma chamber through the plasma port or can reenter the hollow fiber membrane by refiltration for transport out the device through the outlet port.

Prior to use, the plasma chamber is prefilled with plasma chamber solution containing sufficient sorbent particles to bind the plasma component to be separated. The sorbent can be placed in the plasma chamber prior to, simultaneously with, or after filling the plasma chamber with the plasma chamber solution. Such unit is suitable for use as a simultaneous plasma purification and reinfusion system having the above-described advantages.

The removal of heparin from an extracorporeal circuit is a primary objective of the invention. The binding of heparin to a solid substrate by affinity adsorption techniques is documented in the art. E.g., Mohammad et al., Quantitative Removal of Heparin from Plasma and Other Aqueous Solutions by Affinity Adsorption on Poly(L)lysine Sepharose 4B, 20 Thrombosis Res. 599–609 (1980). Poly(L)lysine-coupled agarose beads are one form of preferred sorbent.

The plasma separator device is applicable to any plasma sorbent system where separation, interaction, and recombination takes place. Typical medical procedures where the blood is heparinized include cardiopulmonary bypass, hemodialysis, angioplastic procedures, plasmapheresis, autotransfusion, and hemoconcentration. Exemplary of other potential applications of the system are removal of autoantibodies using sorbents such as immobilized protein A; removal of circulating toxins and tumor antigens using sorbents such as immobilized monoclonal antibodies and specific immobilized ligands; removal of protein-bound toxins and drugs (e.g., in the case of a drug overdose); procedures using live cells in the plasma chamber in the place of sorbents such as islet cells or liver tissue fragments for the treatment of diabetes, hepatocytes for the treatment of liver failure and the like; selective removal of plasma components using immobilized enzymes as sorbents; and removal of cholesterol (low density lipoproteins, LDL) using sorbents specific to LDL.

While not shown in FIG. 2, the hemoconcentrator 88 can be placed in circuit 56 either upstream or downstream of the solute removal device 64. The hemoconcentrator 88 is preferably of a type already known in the art for removing water, fluids, and low molecular weight molecules from blood by ultrafiltration. A preferred hemoconcentrator (FIG. 2) comprises a bundle of hollow fiber ultrafiltration membranes 100 in a housing 104 that defines a chamber in which the hollow fibers are disposed. Inlet 108 and outlet 112 ports are coupled to the bundle of hollow fibers for conducting blood, plasma, or water into and out of the hemoconcentrator. One or more ports 116 and 120 can also be present in the wall of the housing for conducting blood, plasma, or water into or out of the chamber. A vacuum line 124 is also preferably coupled to the hemoconcentrator for removing water therefrom. The vacuum line in FIG. 2 is coupled to a port 120 in the wall of the housing. A collection vessel 128 and vacuum pump 132 are also coupled to the vacuum line. For experimental purposes, pressure ports can be placed at various points in the system for measuring pressure. In FIG. 2, pressure ports 134, 135, 136, 137, and 138 are for measuring, respectively, hemoconcentrator inlet pressure, hemoconcentrator outlet pressure and solute removal device inlet pressure, solute removal device plasma pressure, solute removal device outlet pressure, and hemoconcentrator vacuum pressure. A shunt line 139 from line 52 to line 54 permits the solute removal device 64 to be bypassed. For example, clamping lines 52 and 54 at sites 58 and 60 proximal to the solute removal device permits blood to flow through the shunt line directly from the hemoconcentrator to the blood reservoir. In this configuration, multiple cycles of hemoconcentration can be performed without passing through the solute removal device. Opening such clamps at sites 58 and 60, and clamping the shunt line at site 62 causes the blood to flow through the solute removal device. Thus, the system shown in FIG. 2 permits operation in selected operational modes, such as (1) allowing the blood to flow through the solute removal device each time the blood flows through the hemoconcentrator (simultaneous mode), or (2) allowing the blood to flow through the hemoconcentrator for several cycles and then to flow through the solute removal device (sequential mode).

A preferred hemoconcentrator for use in the present invention is a BIOFILTER 140 (Research Medical, Inc., Midvale, Utah) containing a porous hollow fiber, cellulose diacetate membrane. Other suitable membrane materials include polyacrylonitrile, polysulfone, polymethylmethacrylate, cellulose acetate, cellulose triacetate, and the like. Preferably, the hemoconcentrator is upstream of the solute removal device 64 so that blood passing through the hemoconcentrator is heparinized and has less likelihood of forming clots than if the hemoconcentrator were placed downstream of the solute removal device, particularly where such solute removal device is a heparin removal device. Placing the hemoconcentrator downstream of the heparin removal device increases the likelihood of clots collecting in the hemoconcentrator. Moreover, concentrating the blood also concentrates the targeted solute, e.g. heparin, which makes the solute removal device operate more efficiently.

Although the present invention is shown in reference to a CPB circuit, the invention can also be used by connecting the blood salvage circuit to the cardiotomy circuit or by connecting the blood salvage circuit directly to the patient for processing of patient blood.

Figure 4:
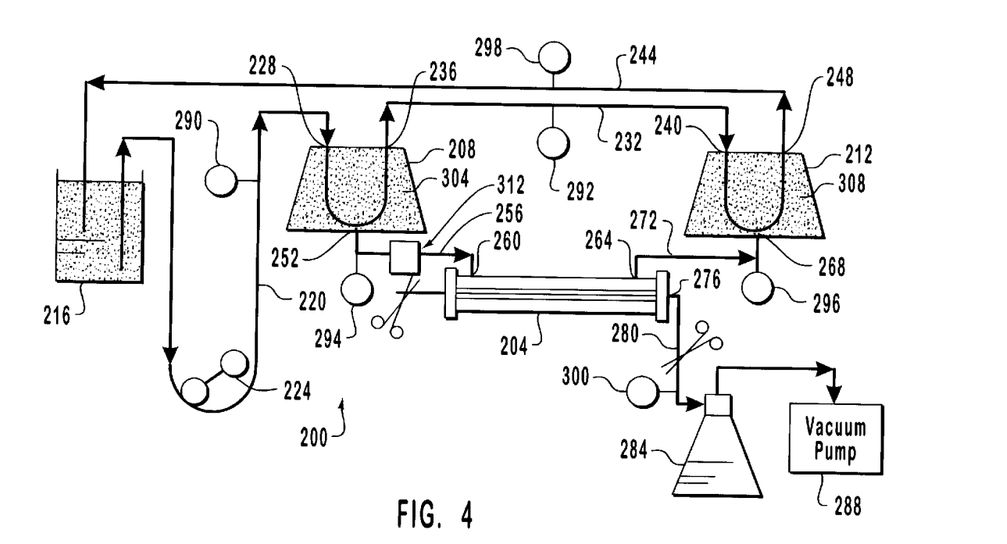
FIG. 4 shows a schematic diagram of another illustrative embodiment of a blood salvage circuit according to the present invention.

Another illustrative embodiment of the present invention is shown in FIG. 4. This system 200 comprises a hemoconcentrator 204 and a pair of selected solute removal devices 208 and 212 coupled to a blood reservoir 216. The blood reservoir could be a cardiotomy reservoir, a CPB circuit, a patient, or the like. The blood reservoir is coupled to device 208 by line 220. A roller pump 224 is disposed on line 220 for pumping the blood through the system. One end of line 220 is coupled to the inlet port 228 of device 208, and the other end of the line 220 is coupled to the blood reservoir. Another line 232 is coupled at one end to the outlet port 236 of device 208 and at the other end to the inlet port 240 of device 212. Line 244 is coupled at one end to the outlet port 248 of device 212 and at the other end to the blood reservoir. The plasma port 252 of device 208 is coupled by line 256 to the inlet port 260 of the hemoconcentrator 204, and the outlet port 264 of the hemoconcentrator is coupled to the plasma port 268 of device 212 by line 272. The vacuum port 276 of the hemoconcentrator 204 is coupled to a vacuum line 280, which is coupled to a collection vessel 284 and a vacuum pump 288. For experimental purposes, pressure ports 290, 292, 294, 296, 298, and 300 are placed in the system as shown for taking pressure measurements. The pressure measurements taken at ports 290, 292, 294, 296, 298, and 300 represent, respectively, pressure at the inlet port 228 of device 208, pressure at the outlet port 236 of device 208 and at the inlet port 240 of device 212, pressure at the plasma chamber 304 of device 208 and pressure of inlet port 260 of the hemoconcentrator 204, pressure at the plasma chamber 308 of device 212, pressure at the outlet port 248 of device 212, and vacuum pressure at the vacuum port 276 of the hemoconcentrator 204. A flow probe 312 in line 256 measures the plasma filtration rate of device 208.

In this configuration, blood is pumped through the first solute removal device 208, and the plasma that is separated from the blood cells is conducted to the hemoconcentrator. In the hemoconcentrator, water and low molecular weight solutes are removed from the plasma and conducted to a collection vessel. The concentrated plasma that exits the hemoconcentrator is then conducted into the plasma chamber of the second solute removal device, where the plasma is combined with blood cells again after refiltration. The blood that exits the second device has thus been subjected to both hemoconcentration and affinity removal of a selected solute.

Not all of the plasma separated from the blood in the first solute removal device 208 passes through the hemoconcentrator. A portion of the plasma reenters the hollow fiber membrane by refiltration for remixing with the blood cells, exits the device at outlet port 236, and is transported through line 232 to the second solute removal device 212. In the second solute removal device 212, the plasma can again pass through the pores in the hollow fiber membranes into the plasma chamber 308. In the plasma chamber 308 there can be mixing of plasma with concentrated plasma from the hemoconcentrator and additional affinity removal of selected solutes. The plasma can then return to the hollow fiber membrane by refiltration, where it is mixed with the blood cells, and eventual returned to the blood reservoir. Preferably, a fine mesh screen is placed at port 252 of device 208 and at port 268 of device 212 to retain sorbent in the plasma chambers.

Figure 5:
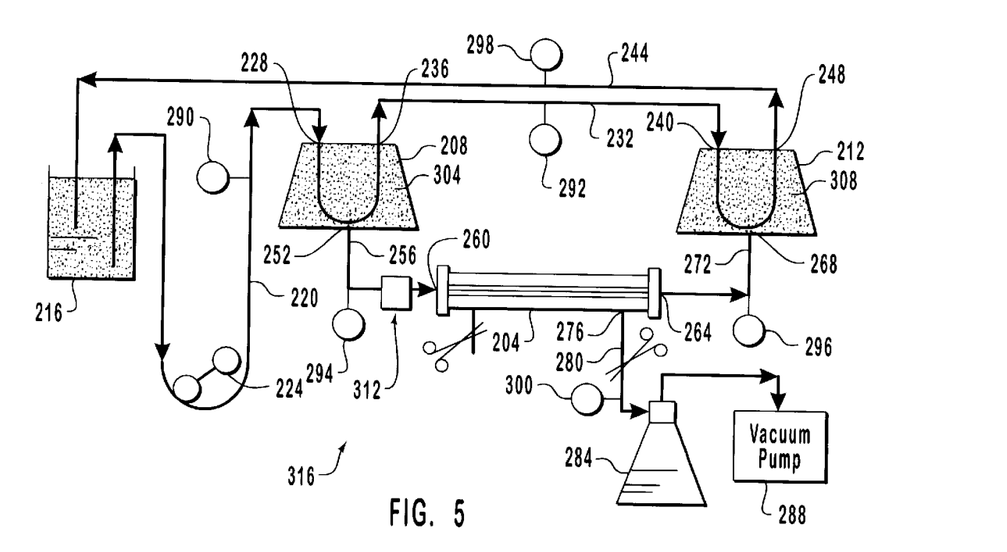
FIG. 5 shows a schematic diagram of still another illustrative embodiment of a blood salvage circuit according to the present invention.

A variant of the embodiment shown in FIG. 4 is illustrated in FIG. 5, where like reference numbers are used to indicate similar parts. The differences between FIG. 4 and FIG. 5 are in how the plasma and the water removed therefrom pass through the hemoconcentrator. In FIG. 4, the plasma enters the hemoconcentrator into the chamber that surrounds the hollow fibers, and the water and low molecular weight solutes pass from the chamber through the pores in the hollow fiber ultrafiltration membrane into the lumens of the hollow fibers and then into the vacuum line for collection in the collection vessel. In contrast, in the system 316 shown in FIG. 5, the plasma enters the hemoconcentrator into the lumens of the hollow fibers, and the water and low molecular weight solutes pass from the lumens of the hollow fibers through the pores in the hollow fibers into the chamber and then into the vacuum line for collection in the collection vessel.

Figure 6:
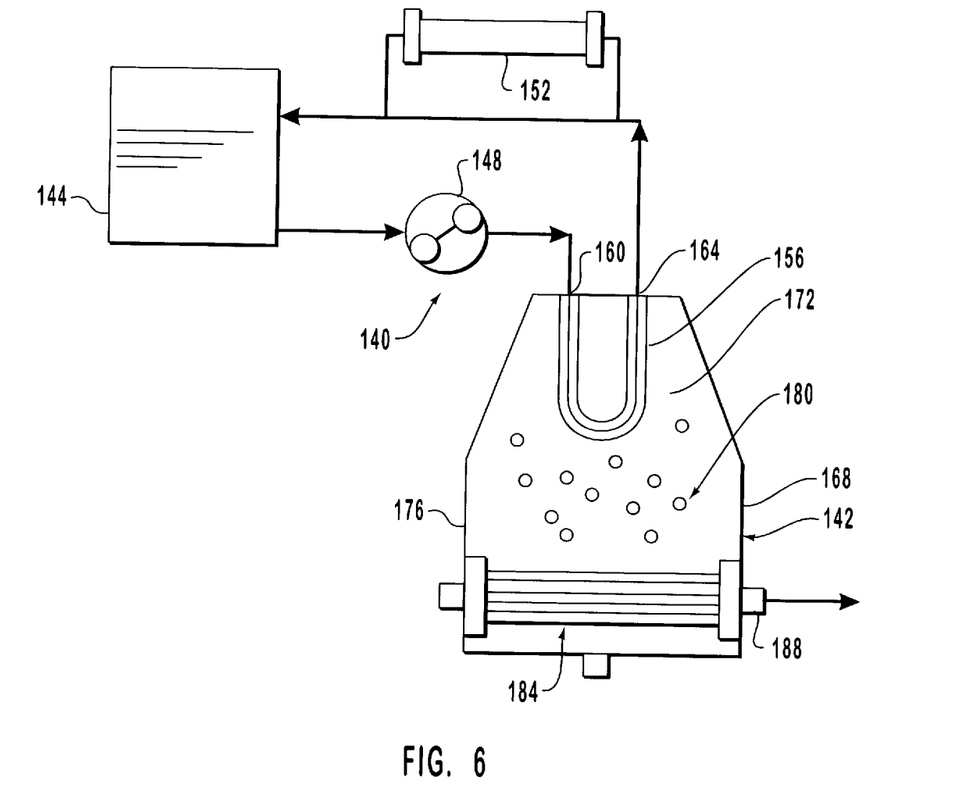
FIG. 6 shows a schematic diagram of a combined device according to the present invention comprising a plasma separator with sorbent for removing selected solutes and an ultrafiltration membrane for hemoconcentration.

In FIG. 6 there is shown a combination device 142 for carrying out the processes of hemoconcentration and selective removal of a targeted solute. The combination device 142 is placed in a blood salvage circuit 140 coupled to a CPB circuit 144, as in FIG. 1. The blood 20 salvage circuit comprises a pump 148 for pumping blood from the CPB circuit 144 through the combination device 142 and optionally through a separate hemoconcentrator 152. The combination device comprises a hollow fiber plasma-separating membrane 156 coupled to an inlet port 160 and an outlet port 164. The hollow fiber plasma-separating membrane 156 is enclosed in a housing 168 that encompasses a plasma chamber 172 containing a plasma chamber solution 176 and a selective sorbent 180. The hollow fibers have pore sizes in the range of about 0.01 $\mu$m to 1.0 $\mu$m, as described above. Also contained within the plasma chamber 172 is an ultrafiltration membrane 184 having an outlet port 188. This ultrafiltration membrane is also made of hollow fibers having a molecular weight cut-off in the range of about 10,000 to 100,000, as described above in connection with the hemoconcentrator. Not only can vacuum be applied to enhance hemoconcentration, but the system also accommodates countervalent or dialysis solutions.

Blood is pumped into the combination device 142 such that the blood enters at the inlet arm 160. The blood passes through the lumens of the hollow fiber membranes, and the plasma and solutes pass through the pores of the membrane into the plasma chamber solution containing a selective sorbent. When selected solutes contact the sorbent, the selected solutes bind to the sorbent, thus depleting the concentration of the selected solute in the plasma. If the outlet port 188 of the ultrafiltration membrane is closed, then the selected-solute-depleted plasma passes through the pores of the hollow fiber plasma-separating membrane 156 by refiltration and passes out of the device 142 into the blood salvage circuit 140. The solute-depleted blood can optionally be passed through a separate hemoconcentrator 152, where water, fluids, and low molecular weight solutes are removed by ultrafiltration, or can pass directly into the CPB circuit 144. In this configuration, the blood can be subjected to simultaneous or sequential hemoconcentration and solute depletion.

By opening the outlet port 188 of the ultrafiltration membrane 184, solute-depleted plasma can be subjected to hemoconcentration in the combination device. Preferably, the outlet port 188 is coupled to a vacuum line, similar to what is shown in FIGS. 2, 4, and 5. Water, fluids, and low molecular weight molecules pass through the ultrafiltration membrane 184 and are drawn out of the device 142 through the outlet port 188 for collection. The pore size of the ultrafiltration membrane 184 can be selected such that the size of the low molecular weight molecules removed is selectable. Typically, the molecular weight cut-off is in the range of about 10,000 to about 100,000. The concentrated plasma in the plasma chamber reenters the hollow fiber plasma-separating membrane 156 by refiltration, mixes with blood cells in the lumens of the hollow fibers, and passes out of the device through the outlet arm 164.

As with the blood salvage circuit of FIGS. 2, 4, and 5, the combination device can be used by connection to the CPB circuit, the cardiotomy circuit, or by connection directly with the patient for processing of patient blood.

The combination device possesses a number of advantages that are not otherwise obtained. For example, the combination device permits blood salvage and targeted solute removal in a single, low cost device. Also, higher pressures can be used for ultrafiltration than are otherwise possible because the ultrafiltration is done in the plasma phase rather than the whole blood phase. Such higher pressures are not possible in the whole blood phase because of the resulting lysis of blood cells. Further, the combination device provides for a quick and easy means for responding to the systemic inflammatory response that accompanies cardiopulmonary bypass in a significant proportion of patients. This systemic inflammatory response is believed to result from the rapid release of certain cytokines into the blood. These cytokines can be removed by using selected sorbents, such as immobilized immunoglobulins, receptors, and/or whole cells, for specific binding of the cytokines. Removal of the cytokines from the blood of a patient undergoing systemic inflammatory response is believed to alleviate such response.

Further advantages of the present invention derive from the lack of high transmembrane pressure in the plasma separating and sorbent-containing device. This relatively low transmembrane pressure results in improved rheology as compared to other devices known in the art such that the present system can be operated at higher flow throughputs. This higher rate of flow results in less time being needed to process the blood, and consequently less time is needed to treat a patient.

Example 1

In this example, pressure and flow data were determined for a plasma separation and sorbent-containing device similar to the plasma sorbent system described in U.S. Pat. No. 5,211,850 to Shettigar & McRea and illustrated in FIG. 3.

In this example, a plasma sorbent system containing a heparin-specific sorbent (HRD, Research Medical Inc., Midvale, Utah) was tested to determine inlet pressure ($P_{in}$), outlet pressure ($P_{out}$), plasma pressure ($P_{plasma}$), and transmembrane pressure (TMP). Pressure measurements were taken at the inlet line 87, outlet line 89, and plasma port 82. TMP was calculated as the average of inlet and plasma pressures less plasma pressure $[(P_{in}+P_{plasma})/2-P_{plasma}]$. Table 1 shows the results of such an experiment using porcine whole blood as the medium. Blood was pumped through the HRD using a SARNS 5000 blood pump.

TABLE 1

| Flow (ml/min) | $P_{in}$ (mm Hg) | $P_{out}$ (mm Hg) | $P_{plasma}$ (mm Hg) | TMP (mm Hg) |
| --- | --- | --- | --- | --- |
| 300 | 210 | 53 | 110 | 50 |
| 400 | 300 | 73 | 160 | 75 |
| 500 | 380 | 95 | 210 | 100 |
| 600 | 475 | 118 | 260 | 110 |
| 700 | 580 | 143 | 335 | 135 |

These data show that the inlet blood pressure ($P_{in}$) increases with the increase in blood flow rate through the hollow fiber lumen. The pressure in the plasma chamber ($P_{plasma}$) also increases proportionately, while the outlet blood pressure ($P_{out}$) increases at a much slower rate. The transmembrane pressure (TMP) is a direct measure of the driving force for the filtration rate of fluid from the blood in the inlet arm of the plasma-separating membrane into the plasma chamber. This driving force is seen to be increasing with the increase in the blood flow rate. This test demonstrates that as the $P_{plasma}$ increases with the increase in $P_{in}$, two different regions of mass transfer are created. In the inlet arm of the plasma-separating membrane where $P_{in} > P_{plasma}$, there is a positive convection of mass transfer across the membrane through its pores into the plasma chamber solution. However, in the outlet arm of the plasma-separating membrane where $P_{out} < P_{plasma}$, this causes a negative or reverse convective mass transfer across the membrane through its pores from the plasma chamber solution into the lumen.

Example 2

In this example, a hemoconcentrator (BIOFILTER 140, Research Medical Inc., Midvale, Utah) was tested to determine vacuum pressure ($P_{vacuum}$), inlet pressure ($P_{in}$), outlet pressure ($P_{out}$), transmembrane pressure (TMP), and ultrafiltration rate (UFR) at three different flow rates using human blood in human clinical trials. TMP was determined as the average of inlet and outlet pressures less vacuum pressure $[(P_{in}+P_{out})/2-P_{vacuum}]$. Blood was pumped with a roller pump from a cardiotomy reservoir or cardiopulmonary bypass circuit into the hemoconcentrator through the inlet port. Water and solutes having a molecular weight lower than that of the molecular weight cut-off of the ultrafiltration membrane passed from the lumens of the hollow fibers through the pores of the membrane into the chamber defined by the housing. A vacuum line was coupled to a port in the housing and to a collection flask and a vacuum pump for applying reduce pressure to the chamber. Concentrated whole blood passed through the outlet port for return to the cardiotomy reservoir or CPB circuit. Tables 2–4 show the results of such experiments at hemoconcentrator flow rates of 200 ml/min, 300 ml/min, and 400 ml/min, respectively.

TABLE 2

| Hemoconcentrator Flow Rate = 200 ml/min | | | | |
| --- | --- | --- | --- | --- |
| $P_{vacuum}$ (mm Hg) | $P_{in}$ (mm Hg) | $P_{out}$ (mm Hg) | TMP (mm Hg) | UFR (ml/min) |
| 0 | 74 | 21 | 51 | 12 |
| −66 | 74 | 20 | 113 | 50 |
| −147 | 71 | 15 | 190 | 81 |
| −205 | 96 | 20 | 262 | 88 |
| −260 | 103 | 21 | 322 | 98 |
| −349 | 105 | 21 | 412 | 102 |

TABLE 3

| Hemoconcentrator Flow Rate = 300 ml/min | | | | |
| --- | --- | --- | --- | --- |
| $P_{vacuum}$ (mm Hg) | $P_{in}$ (mm Hg) | $P_{out}$ (mm Hg) | TMP (mm Hg) | UFR (ml/min) |
| −64 | 92 | 21 | 121 | 59 |
| −147 | 92 | 21 | 204 | 92 |
| −228 | 108 | 21 | 293 | 126 |
| −343 | 109 | 21 | 407 | 139 |

TABLE 4

| Hemoconcentrator Flow Rate = 400 ml/min | | | | |
| --- | --- | --- | --- | --- |
| $P_{vacuum}$ (mm Hg) | $P_{in}$ (mm Hg) | $P_{out}$ (mm Hg) | TMP (mm Hg) | UFR (ml/min) |
| −42 | 120 | 22 | 114 | 43 |
| −122 | 124 | 11 | 195 | 87 |
| −218 | 123 | 20 | 289 | 115 |
| −313 | 137 | 22 | 392 | 139 |
| −386 | 227 | 16 | 508 | 128 |

These results show ultrafiltration rates can be manipulated by varying flow rates and vacuum pressures. At a given flow rate, the ultrafiltration rate can generally be increased by increasing the vacuum pressure.

Example 3

This example shows an illustrative embodiment of the present invention according to the system shown in FIG. 2, wherein hemoconcentration and heparin removal were carried out simultaneously. The hemoconcentrator was a BIOFILTER 140 and the solute removal device was an HRD for removing heparin. The shunt line was clamped such that blood passed through the hemoconcentrator and the solute removal device in each passage through the circuit.

In this example, bovine whole blood was recirculated through the system at a flow rate of 500 ml/min for 60 minutes. The pressure, ultrafiltration rate, and heparin removal data from this experiment are shown in Table 5.

TABLE 5

|  | Example 3 | Example 4 | Example 5 |
| --- | --- | --- | --- |
| Hemo $P_{in}$ (mm Hg) | 538 | 238 | NA |
| Hemo $P_{out}$/HRD $P_{in}$ (mm Hg) | 348 | 42 | 314 |

TABLE 5-continued

|  | Example 3 | Example 4 | Example 5 |
|---|---|---|---|
| HRD $P_{out}$ (mm Hg) | 2 | NA | 290 |
| HRD $P_{plasma}$ (mm Hg) | 131 | NA | −34 |
| $P_{vacuum}$ (mm Hg) | NA | −172 | −300 |
| Hemo TMP (mm Hg) | 477 | 312 | NA |
| HRDTMP(mm Hg) | 118 | 118 | 162 |
| UFR (ml/min) | 122 | 95 | 15 |
| % Heparin Removed/Pass | 15 | 16 | 17 |

Example 4

This example shows an illustrative embodiment of the present invention according to the system shown in FIG. 2 and according to the procedure of Example 3 except that at the beginning of the experiment the shunt was used to bypass the heparin removal device until a selected volume was removed, and then the blood was caused to circulate through the heparin removal device. Thus, this example shows that hemoconcentration and heparin removal can be carried out sequentially. It is preferred to perform the hemoconcentration prior to heparin removal, because performing heparin removal prior to hemoconcentration leads to a greater likelihood of clot formation.

In this example, bovine whole blood was recirculated through the system at a flow rate of 500 ml/min for 60 minutes. The pressure, ultrafiltration rate, and heparin removal data from this experiment are shown in Table 5.

Example 5

This example shows an illustrative embodiment of the present invention according to the system shown in FIG. 6, wherein hemoconcentration and selected solute removal were carried out in a single device combining a hemoconcentrator and a solute removal device. Pressure measurements were taken so that inlet pressure ($P_{in}$), plasma chamber pressure ($P_{plasma}$), outlet pressure ($P_{out}$), and vacuum pressure ($P_{vacuum}$) were determined.

In this example, bovine whole blood was recirculated through the system at a flow rate of 500 ml/min for 60 minutes. The pressure, ultrafiltration rate, and heparin removal data from this experiment are shown in Table 5.

Example 6

This example shows an illustrative embodiment of the present invention according to the system shown in FIG. 4. Pressure measurements were taken at ports 290, 292, 294, 296, 298, and 300, which represent, respectively, pressure at the inlet port of device 208, pressure at the outlet port of device 208 and at the inlet port of device 212, pressure at the plasma chamber of device 208, pressure at the plasma chamber of device 212, pressure at the outlet port of device 212, and vacuum pressure at the vacuum port of the hemoconcentrator. A flow probe 312 in line 256 measured the plasma filtration rate of device 208.

In this example, 3 liters of bovine whole blood at 30° C. and a hematocrit of 0.26 was used in the system. The roller pump was a Masterflex Model 7524-00, and the vacuum pump was a GAST Model DOA-P104-AA. The selected solute removal devices were heparin removal devices (HRD, Research Medical Inc.), and the hemoconcentrator was a Biofilter 140 (Research Medical Inc.). Tygon tubing (S-50-HL Class VI, 6.35 mm×1.59 mm and 4.77 mm×1.59 mm). The flow probe was a Transonic flow probe No. H6X117 used with a Transonic HT109R flowmeter and 6.35 mm×1.59 mm tubing. Pressure measurements were taken with a Deltran Disposable Pressure Transducer (Utah Medical, Midvale, Utah). Data collection was with an HP 75000 system.

The results of these experiments are shown in Tables 6 and 7.

TABLE 6

| Vacuum Port condition | Blood flow ml/min | P1 mm Hg | P2 mm Hg | P3 mm Hg | Plasma flow F1 ml/min | P4 mm Hg | P5 mm Hg | P6 mm Hg | Water flow ml/min |
|---|---|---|---|---|---|---|---|---|---|
| Vac Closed | 200 | 190 | 98 | 47 | 45 | 39 | 4 | 1 | 0 |
| Open to air | 200 | 191 | 98 | 39 | 38 | 35 | 3 | 4 | 13 |
| −100 mm Hg | 200 | 197 | 103 | 36 | 34 | 30 | 4 | −95 | 48 |
| −200 mm Hg | 200 | 202 | 108 | 11 | 35 | 12 | 4 | −201 | 67 |
| −300 mm Hg | 200 | 216 | 115 | −23 | 42 | −18 | 4 | −309 | 95 |
| −400 Hg | 200 | 211 | 114 | −78 | 52 | −76 | 4 | −406 | 100 |
| Vac Closed | 400 | 441 | 231 | 112 | 64 | 104 | 9 | 3 | 0 |
| Open to air | 400 | 444 | 229 | 98 | 68 | 90 | 9 | 4 | 45 |
| −100 mm Hg | 400 | 451 | 235 | 107 | 66 | 103 | 9 | −107 | 75 |
| −200 mm Hg | 400 | 463 | 239 | 68 | 73 | 69 | 8 | −195 | 100 |
| −300 mm Hg | 400 | 476 | 246 | 57 | 76 | 59 | 8 | −307 | 120 |
| −400 mm Hg | 400 | 472 | 251 | 39 | 77 | 43 | 8 | −410 | 145 |
| Vac Closed | 500 | 578 | 306 | 127 | 71 | 133 | 11 | 1 | 0 |
| Open to air | 500 | 588 | 301 | 109 | 76 | 115 | 11 | 1 | 50 |
| −100 mm Hg | 500 | 600 | 310 | 97 | 78 | 106 | 11 | −98 | 75 |
| −200 mm Hg | 500 | 600 | 313 | 81 | 80 | 93 | 11 | −203 | 105 |
| −300 mm Hg | 500 | 606 | 316 | 75 | 79 | 88 | 10 | −292 | 125 |
| −400 mm Hg | 500 | 608 | 316 | 58 | 81 | 70 | 10 | −395 | 150 |
| Vac Closed | 600 | 733 | 392 | 173 | 101 | 177 | 14 | −1 | 0 |
| Open to air | 600 | 719 | 380 | 157 | 102 | 162 | 13 | −3 | 60 |
| −100 mm Hg | 600 | 714 | 369 | 127 | 104 | 135 | 13 | −99 | 90 |
| −200 mm Hg | 600 | 704 | 360 | 109 | 102 | 121 | 12 | −195 | 110 |
| −300 mm Hg | 600 | 745 | 382 | 126 | 117 | 123 | 13 | −298 | 135 |
| −400 mm Hg | 600 | 751 | 383 | 117 | 116 | 115 | 13 | −403 | 170 |
| Vac closed | 700 | 869 | 454 | 237 | 134 | 227 | 14 | −2 | 0 |

TABLE 6-continued

| Vacuum Port condition | Blood flow ml/min | P1 mm Hg | P2 mm Hg | P3 mm Hg | Plasma flow F1 ml/min | P4 mm Hg | P5 mm Hg | P6 mm Hg | Water flow ml/min |
|---|---|---|---|---|---|---|---|---|---|
| Open to air | 700 | 858 | 445 | 190 | 122 | 185 | 14 | −2 | 75 |
| −100 mm Hg | 700 | 870 | 446 | 180 | 129 | 175 | 15 | −97 | 105 |
| −200 mm Hg | 700 | 864 | 442 | 167 | 134 | 162 | 15 | −204 | 130 |
| −300 mm Hg | 700 | 867 | 438 | 158 | 137 | 153 | 15 | −305 | 155 |
| −400 mm Hg | 700 | 902 | 462 | 152 | 139 | 147 | 15 | −402 | 175 |

TABLE 7

| Vacuum Port condition | Blood flow ml/min | TMP of HRD #1 mm Hg | TMP of HRD #2 mm Hg | TMP of Hemoconc. mm Hg | Vol. percentage water flow to blood flow % | Vol. percentage Plasma flow to blood flow % | Estimated Hct of the exit blood after 1st pass |
|---|---|---|---|---|---|---|---|
| Vac Closed | 200 | 72 | 30 | 42 | 0 | 23 | 0.26 |
| Open to air | 200 | 76 | 32 | 33 | 7 | 19 | 0.28 |
| −100 mm Hg | 200 | 81 | 37 | 128 | 24 | 17 | 0.34 |
| −200 mm Hg | 200 | 95 | 48 | 213 | 33 | 18 | 0.39 |
| −300 mm Hg | 200 | 119 | 67 | 288 | 48 | 21 | 0.50 |
| −400 Hg | 200 | 144 | 95 | 329 | 50 | 26 | 0.52 |
| Vac Closed | 400 | 165 | 63 | 105 | 0 | 16 | 0.26 |
| Open to air | 400 | 173 | 70 | 90 | 11 | 17 | 0.29 |
| −100 mm Hg | 400 | 172 | 66 | 211 | 19 | 16 | 0.32 |
| −200 mm Hg | 400 | 198 | 85 | 264 | 25 | 18 | 0.35 |
| −300 mm Hg | 400 | 210 | 94 | 365 | 30 | 19 | 0.37 |
| −400 mm Hg | 400 | 222 | 104 | 451 | 36 | 19 | 0.41 |
| Vac Closed | 500 | 226 | 87 | 129 | 0 | 14 | 0.26 |
| Open to air | 500 | 239 | 93 | 111 | 10 | 15 | 0.29 |
| −100 mm Hg | 500 | 251 | 102 | 200 | 15 | 16 | 0.31 |
| −200 mm Hg | 500 | 259 | 110 | 290 | 21 | 16 | 0.33 |
| −300 mm Hg | 500 | 265 | 114 | 374 | 25 | 16 | 0.35 |
| −400 mm Hg | 500 | 275 | 123 | 458 | 30 | 16 | 0.37 |
| Vac Closed | 600 | 280 | 108 | 176 | 0 | 17 | 0.26 |
| Open to air | 600 | 281 | 109 | 163 | 10 | 17 | 0.29 |
| −100 mm Hg | 600 | 294 | 117 | 230 | 15 | 17 | 0.31 |
| −200 mm Hg | 600 | 297 | 119 | 310 | 18 | 17 | 0.32 |
| −300 mm Hg | 600 | 310 | 129 | 423 | 23 | 19 | 0.34 |
| −400 mm Hg | 600 | 317 | 134 | 518 | 28 | 19 | 0.36 |
| Vac Closed | 700 | 316 | 113 | 234 | 0 | 16 | 0.26 |
| Open to air | 700 | 334 | 130 | 190 | 11 | 17 | 0.29 |
| −100 mm Hg | 700 | 345 | 135 | 275 | 15 | 18 | 0.31 |
| −200 mm Hg | 700 | 349 | 140 | 368 | 19 | 19 | 0.32 |
| −300 mm Hg | 700 | 354 | 142 | 461 | 22 | 20 | 0.33 |
| −400 mm Hg | 700 | 375 | 158 | 552 | 25 | 20 | 0.35 |

Example 7

In this example, the system was configured according to FIG. 5, and the procedure was as in Example 6. The results were similar to those of Example 6.

We claim:

1. A system for salvaging blood from a patient for the selective removal of a targeted solute in the blood and the removal of water, fluids, and low molecular weight solutes comprising:

(a) a hemoconcentrator comprising an inlet port, and outlet port, and a porous ultrafiltration membrane having a selected molecular weight cut-off for retaining components selected from the group consisting of cells and solutes with a molecular weight greater than the cut-off and for allowing water, fluids, and solutes with a molecular weight less than the cut-off to be removed from blood or plasma; and (b) a first solute removal device for selectively removing the targeted solute from blood by means of convective and diffusive transport of plasma from said blood across a hollow fiber plasma-separating membrane into a closed plasma chamber where the selective removal of the targeted solute from non-targeted solutes using a sorbent is accomplished followed by the subsequent transport of the non-targeted solutes across the hollow fiber plasma-separating membrane back into the blood, comprising (i) the closed plasma chamber configured for being filled with a plasma chamber solution and to freely circulate, equilibrate, and interact plasma in said plasma chamber solution under relatively uniform pressure;

(ii) the hollow fiber plasma-separating membrane, wherein said hollow fiber plasma-separating membrane has an inlet arm and an outlet arm and is configured for being immersed in said plasma chamber solution in said closed plasma chamber;

(iii) at least one sorbent having an affinity for binding said targeted solute, wherein said sorbent is contained in said closed plasma chamber;

(iv) means for securing said inlet arm and outlet arm of said hollow fiber plasma-separating membrane in said closed plasma chamber; and (v) means for circulating said blood into said inlet arm, through said hollow fiber plasma-separating membrane, and out through said outlet arm; and (c) means for coupling said hemoconcentrator to said first solute removal device to permit liquid communication therebetween and for coupling said hemoconcentrator and said first solute removal device to said patient to permit blood to be received from and returned to said patient.

2. The system of claim 1 wherein said porous ultrafiltration membrane of said hemoconcentrator comprises a plurality of hollow fibers.

3. The system of claim 2 wherein the molecular weight cut-off of said porous ultrafiltration membrane is in the range of about 10,000 to 100,000.

4. The system of claim 3 wherein said porous ultrafiltration membrane is made from a material selected from the group consisting of polyacrylonitrile, polysulfone, polynethylmethacrylate, cellulose acetate, cellulose diacetate, and cellulose triacetate.

5. The system of claim 1 wherein said hollow fiber plasma-separating membrane comprises a bundle of parallel hollow fibers.

6. The system of claim 5 wherein said sorbent is of a size and configuration such that said sorbent is not permeable to the hollow fiber plasma-separating membrane.

7. The system of claim 6 wherein said hollow fibers making up said hollow fiber plasma-separating membrane are constructed of a blood-compatible material having a suitable pore size to allow passage of plasma into the plasma chamber solution while retaining blood cells and platelets from the blood within the hollow fibers.

8. The system of claim 7 wherein the pore sizes in said hollow fibers of said hollow fiber plasma-separating membrane range between about 0.01 $\mu$m to 1.0 $\mu$m.

9. The system of claim 8 wherein said hollow fibers of said hollow fiber plasma-separating membrane are made from a material selected from the group consisting of polypropylene, cellulose diacetate, polycarbonate, polyvinylchloride, polyvinylalcohol, polymethylmethacrylate, polyethylene, polysulfone, and polyethylenevinylalcohol.

10. The system according to claim 9 wherein the sorbent comprises a ligand immobilized on a substrate and said ligand is a member selected from the group consisting of enzymes, living tissue, fragments of tissue, cells, antibodies, peptides, macromolecules, nucleic acids, lectins, carbohydrates, and chelating agents.

11. The system of claim 10 wherein said sorbent has affinity for heparin.

12. The system of claim 11 wherein the substrate is agarose.

13. The system of claim 12 wherein the sorbent is poly-L-lysine-coupled agarose.

14. The system of claim 1 wherein said hemoconcentrator is disposed within said closed plasma chamber of said first solute removal device in fluid communication with said plasma chamber solution to thereby effect simultaneous hemoconcentration and removal of the targeted solute.

15. The system of claim 1 wherein said hemoconcentrator is disposed in fluid communication with said first solute removal device such that said blood is permitted to pass from said hemoconcentrator to said first solute removal device, or vice-versa, to thereby effect sequential hemoconcentration and removal of the targeted solute or sequential removal of the targeted solute and hemoconcentration, respectively.

16. The system of claim 1 wherein said outlet port of said hemoconcentrator is coupled to the inlet arm of said first solute removal device such that blood passes through said hemoconcentrator for removal of water, fluids, and low molecular weight solutes to result in concentrated blood, which concentrated blood then passes through said first solute removal device for removal of the targeted solute.

17. The system of claim 1 wherein the outlet arm of said first solute removal device is coupled to the inlet port of said hemoconcentrator such that blood passes through said first solute removal device for removal of the targeted solute resulting in targeted-solute-depleted blood, which targeted-solute-depleted blood then passes through said hemoconcentrator for removal of water, fluids, and low molecular weight solutes.

18. The system of claim 1 wherein said plasma chamber solution is an electrolyte.

19. The system of claim 1 wherein said porous ultrafiltration membrane is contained in said closed plasma chamber such that water, fluids, and low molecular weight solutes can be removed from said plasma by ultrafiltration.

20. The system of claim 1 further comprising a second solute removal device, which comprises (i) A closed plasma chamber configured for being filled with a plasma chamber solution and to freely circulate, equilibrate, and interact plasma in said plasma chamber solution under relatively uniform pressure;

(ii) a hollow fiber plasma-separating membrane, wherein said hollow fiber plasma-separating membrane has an inlet arm and an outlet arm and is configured for being immersed in said plasma chamber solution in said closed plasma chamber;

(iii) at least one sorbent having an affinity for binding said targeted solute, wherein said sorbent is contained in said closed plasma chamber;

(iv) means for securing said inlet arm and outlet arm of said hollow fiber plasma-separating membrane in said closed plasma chamber; and (v) means for circulating blood into said inlet arm, through said hollow fiber plasma-separating membrane, and out through said outlet arm; wherein the closed plasma chamber of said first solute removal device is coupled to the inlet port of said hemoconcentrator and the outlet port of said hemoconcentrator is coupled to the closed plasma chamber of said second solute removal device such that plasma can flow from said first solute removal device through said hemoconcentrator to said second solute removal device such that water, fluids, and low molecular weight solutes can be removed from said plasma by ultrafiltration, and wherein said outlet arm of said first solute removal device is coupled to the inlet arm of said second solute removal device such that blood can flow therebetween.

21. An apparatus for selectively removing a targeted solute from blood by binding said targeted solute to an affinity sorbent and removing water, fluids, and low molecular weight solutes by ultrafiltration, comprising:

(a) a closed plasma chamber configured for being filled with a plasma chamber solution and to freely circulate, equilibrate, and interact plasma in said plasma chamber solution under relatively uniform pressure;

(b) a hollow fiber plasma-separating membrane having an inlet arm and an outlet arm and configured for being immersed in said plasma chamber solution in said closed plasma chamber;

(c) at least one sorbent having an affinity for binding said targeted solute, wherein said sorbent is contained in said closed plasma chamber;

(d) means for securing said inlet arm and outlet arm of said hollow fiber plasma-separating membrane in said close plasma chamber; and (e) a porous ultrafiltration membrane disposed in said closed plasma chamber and configured for being immersed in said plasma chamber solution, said ultrafiltration membrane having a selected molecular weight cut-off for allowing water, fluids, and solutes with a molecular weight lower than the cut-off and means for withdrawing said water, fluids, and solutes that pass through said ultrafiltration membrane; and (f) means for circulating said blood into said inlet arm such that plasma, including water, fluids, and low molecular weight solutes therein, is transported from said blood across said hollow fiber plasma-separating membrane by convective and diffusive transport into the plasma chamber solution where the selective removal of the targeted solute from non-targeted solutes using said affinity sorbent is accomplished followed by the subsequent transport of the non-targeted solutes across the hollow fiber plasma-separating membrane back into the blood and out through said outlet arm.

22. A system for salvaging blood from a patient for the selective removal of a targeted solute in the blood and the removal of water, fluids, and low molecular weight solutes comprising:

(a) a hemoconcentrator comprising an inlet port, an outlet port, and a porous ultrafiltration membrane having a selected molecular weight cut-off for retaining components selected from the group consisting of cells and solutes with a molecular weight greater than the cut-off and for allowing water, fluids, and solutes with a molecular weight less than the cut-off to be removed from blood or plasma; and (b) first and second solute removal devices for selectively removing the targeted solute from blood by means of convective and diffusive transport of plasma from said blood across a hollow fiber plasma-separating membrane into a closed plasma chamber where the selective removal of the targeted solute from non-targeted solutes using a sorbent is accomplished followed by the subsequent transport of the non-targeted solutes across the hollow fiber plasma-separating membrane back into the blood, each said first and second solute removal device comprising (i) the closed plasma chamber configured for being filled with a plasma chamber solution and to freely circulate, equilibrate, and interact plasma in said plasma chamber solution under relatively uniform pressure;

(ii) the hollow fiber plasma-separating membrane, wherein said hollow fiber plasma-separating membrane has an inlet aim and an outlet arm and is configured for being immersed in said plasma chamber solution in said closed plasma chamber;

(iii) at least one sorbent having an affinity for binding said targeted solute, wherein said sorbent is contained in said closed plasma chamber;

(iv) means for securing said inlet arm and outlet arm of said hollow fiber plasma-separating membrane in said closed plasma chamber; and (v) means for circulating said blood into said inlet arm, through said hollow fiber plasma-separating membrane, and out through said outlet arm;

(c) means for coupling the closed plasma chamber of said first solute removal device to the inlet port of said hemoconcentrator and means for coupling the outlet port of said hemoconcentrator to the closed plasma chamber of said second solute removal device such that plasma can flow from said first solute removal device through said hemoconcentrator to said second solute removal device such that water, fluids, and low molecular weight solutes can be removed from said plasma by ultrafiltration, and means for coupling the outlet arm of said first solute removal device to the inlet arm of said second solute removal device such that blood can flow therebetween; and (d) means for coupling said first and second solute removal devices to said patient to permit blood to be received from and returned to said patient.

23. A method of selectively removing a targeted solute and water, fluids, and low molecular weight solutes from blood comprising:

(a) providing a system comprising:

(1) a hemoconcentrator comprising an inlet port, an outlet port, and a porous ultrafiltration membrane having a selected molecular weight cut-off for retaining components selected from the group consisting of cells and solutes with a molecular weight greater than the cut-off and for allowing water, fluids, and solutes with a molecular weight less than the cut-off to be removed from blood or plasma; and (2) a first solute removal device for selectively removing the targeted solute from blood by means of convective and diffusive transport of plasma from said blood across a hollow fiber plasma-separating membrane into a closed plasma chamber where the selective removal of the targeted solute from non-targeted solutes using a sorbent is accomplished followed by the subsequent transport of the non-targeted solutes across the hollow fiber plasma-separating membrane back into the blood, comprising (i) the closed plasma chamber configured for being filled with a plasma chamber solution and to freely circulate, equilibrate, and interact plasma in said plasma chamber solution under relatively uniform pressure;

(ii) the hollow fiber plasma-separating membrane, wherein said hollow fiber plasma-separating membrane has an inlet arm and an outlet arm and is configured for being immersed in said plasma chamber solution in said closed plasma chamber;

(iii) at least one sorbent having an affinity for binding said targeted solute, wherein said sorbent is contained in said closed plasma chamber;

(iv) means for securing said inlet arm and outlet arm of said hollow fiber plasma-separating membrane in said closed plasma chamber; and (v) means for circulating said blood into said inlet arm, through said hollow fiber plasma-separating membrane, and out through said outlet arm; and (3) means for coupling said hemoconcentrator to said first solute removal device to permit liquid communication therebetween and for coupling said hemoconcentrator and said first solute removal device to a blood source to permit blood to be received from and returned to said blood source;

(b) directing said blood from said blood source into said inlet arm by said means for circulating said blood, through said hollow fiber plasma-separating membrane and out said outlet arm at a volume and a velocity that permits convective and convective and diffusive transport of plasma from said blood across said hollow fiber plasma-separating membrane along the inlet arm of said hollow fiber plasma-separating membrane into said plasma chamber solution;

(c) causing said plasma in said plasma chamber solution to come into contact with said sorbent such that said targeted solute is selectively bound to said sorbent;

(d) causing said non-targeted solutes to pass by diffusive and convective transport from said plasma chamber solution across the hollow fiber plasma-separating membrane into the blood retained by said hollow fiber plasma-separating membrane and out of said first solute removal device;

(e) causing said blood or plasma to pass through said hemoconcentrator such that water, fluids, and solutes with a molecular weight less than said cut-off pass through said porous ultrafiltration membrane and are withdrawn from said blood or plasma, and said ultrafiltration retains cells and solutes with a molecular weight greater than said cut-off in said blood or plasma.

24. The method of claim 23 wherein said porous ultrafiltration membrane of said hemoconcentrator comprises a plurality of hollow fibers.

25. The method of claim 24 wherein the molecular weight cut-off of said porous ultrafiltration membrane is in the range of about 10,000 to 100,000.

26. The method of claim 25 wherein said porous ultrafiltration membrane is made from a material selected from the group consisting of polyacrylonitrile, polysulfone, polyethylmethacrylate, cellulose acetate, cellulose diacetate, and cellulose triacetate.

27. The method of claim 23 wherein said hollow fiber plasma-separating membrane comprises a bundle of parallel hollow fibers.

28. The method of claim 27 wherein said sorbent is of a size and configuration such that said sorbent is not permeable to the hollow fiber plasma-separating membrane.

29. The method of claim 28 wherein said hollow fibers making up said hollow fiber plasma-separating membrane are constructed of a blood-compatible material having a suitable pore size to allow passage of plasma into the plasma chamber solution while retaining blood cells and platelets from the blood within the hollow fibers.

30. The method of claim 29 wherein the pore sizes in said hollow fibers of said hollow fiber plasma-separating membrane range between about 0.01 $\mu$m to 1.0 $\mu$m.

31. The method of claim 30 wherein said hollow fibers of said hollow fiber plasma-separating membrane are made from a material selected from the group consisting of polypropylene, cellulose diacetate, polycarbonate, polyvinylchloride, polyvinylalcohol, polymethylmethacrylate, polyethylene, polysulfone, and polyethylenevinylalcohol.

32. The method according to claim 31 wherein the sorbent comprises a ligand immobilized on a substrate and said ligand is a member selected from the group consisting of enzymes, living tissue, fragments of tissue, cells, antibodies, peptides, macromolecules, nucleic acids, lectins, carbohydrates, and chelating agents.

33. The method of claim 32 wherein said sorbent has affinity for heparin.

34. The method of claim 33 wherein the substrate is agarose.

35. The method of claim 34 wherein the sorbent is poly-L-lysine-coupled agarose.

36. The method of claim 23 wherein said hemoconcentrator is disposed within said closed plasma chamber of said first solute removal device in fluid communication with said plasma chamber solution to thereby effect simultaneous hemoconcentration and removal of the targeted solute.

37. The method of claim 23 wherein said hemoconcentrator is disposed in fluid communication with said first solute removal device such that said blood is permitted to pass from said hemoconcentrator to said first solute removal device, or vice versa, to thereby effect sequential hemoconcentration and removal of the targeted solute or sequential removal of the targeted solute and hemoconcentration, respectively.

38. The method of claim 23 wherein said outlet port of said hemoconcentrator is coupled to the inlet arm of said first solute removal device such that blood passes through said hemoconcentrator for removal of water, fluids, and low molecular weight solutes to result in concentrated blood, which concentrated blood then passes through said first solute removal device for removal of the targeted solute.

39. The method of claim 23 wherein said outlet arm of said first solute removal device is coupled to the inlet port of said hemoconcentrator such that blood passed through said first solute removal device for removal of the targeted solute resulting in targeted-solute-depleted blood, which targeted-solute-depleted blood then passes through said hemoconcentrator for removal of water, fluids, and low molecular weight solutes.

40. The method of claim 23 wherein said plasma chamber solution is an electrolyte.

41. The method of claim 23 wherein said porous ultrafiltration membrane is contained in said closed plasma chamber such that water, fluids, and low molecular weight solutes can be removed from said plasma by ultrafiltration.

42. The method of claim 23 further comprises a second solute removal device, which comprises (i) a closed plasma chamber configured for being filled with a plasma chamber solution and to freely circulate, equilibrate, and interact plasma in said plasma chamber solution under relatively uniform pressure;

(ii) a hollow fiber plasma-separating membrane, herein said hollow fiber plasma-separating membrane has an inlet arm and an outlet arm and is configured for being immersed in said plasma chamber solution in said closed plasma chamber;

(iii) at least one sorbent having an affinity for binding said targeted solute, wherein said sorbent is contained in said closed plasma chamber;

(iv) means for securing said inlet arm and outlet arm of said hollow fiber plasma-separating membrane in said closed plasma chamber; and (v) means for circulating blood into said inlet arm, through said hollow fiber plasma-separating membrane, and out through said outlet arm; wherein the closed plasma chamber of said first solute removal device is coupled to the inlet port of said hemoconcentrator and the outlet port of said hemoconcentrator is coupled to the closed plasma chamber of said second solute removal device such that plasma can flow from said first solute removal device through said hemoconcentrator to said second solute removal device such that water, fluids, and low molecular weight solutes can be removed from said plasma by ultrafiltration, and wherein said outlet arm of said first solute removal device is coupled to the inlet arm of said second solute removal device such that blood can flow therebetween.

* * * * *